(12) United States Patent
Bose et al.

(10) Patent No.: US 9,333,211 B2
(45) Date of Patent: May 10, 2016

(54) PHOSPHAPLATIN MEDIATED MODULATION OF PIGMENT EPITHELIAL DERIVED FACTOR AND USES THEREOF

(71) Applicants: Rathindra N. Bose, Houston, TX (US); Shadi Moghaddas, Pearland, TX (US); Homa Dezvareh, Houston, TX (US)

(72) Inventors: Rathindra N. Bose, Houston, TX (US); Shadi Moghaddas, Pearland, TX (US); Homa Dezvareh, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 14/186,245

(22) Filed: Feb. 21, 2014

(65) Prior Publication Data
US 2014/0243293 A1    Aug. 28, 2014

Related U.S. Application Data

(60) Provisional application No. 61/768,036, filed on Feb. 22, 2013.

(51) Int. Cl.
| | | |
|---|---|---|
| *A61K 31/675* | (2006.01) | |
| *A61K 31/555* | (2006.01) | |
| *A61K 31/6615* | (2006.01) | |

(Continued)

(52) U.S. Cl.
CPC ............ *A61K 31/6615* (2013.01); *A61K 31/255* (2013.01); *A61K 31/337* (2013.01); *A61K 31/427* (2013.01); *A61K 31/519* (2013.01); *A61K 31/555* (2013.01); *A61K 31/675* (2013.01); *A61K 31/69* (2013.01); *A61K 33/24* (2013.01); *A61K 45/06* (2013.01)

(58) Field of Classification Search
CPC ............ A61K 31/555; A61K 31/6615; A61K 31/675; A61K 33/24
See application file for complete search history.

(56) References Cited

FOREIGN PATENT DOCUMENTS

| WO | WO 2009/021081 A1 | * | 2/2009 |
|---|---|---|---|
| WO | WO 2011/153365 | * | 12/2011 |
| WO | WO 2012/096722 | * | 7/2012 |

OTHER PUBLICATIONS

Tombran-Tink J, Mazuruk K, Rodriguez IR, Chung D, Linker T, Englander E, Chader GJ. Organization, evolutionary conservation, expression and unusual Alu density of the human gene for pigment epithelium-derived factor, a unique neurotrophic serpin. Mol Vis. Nov. 4, 1996;2:11.

(Continued)

*Primary Examiner* — Valerie Rodriguez-Garcia
(74) *Attorney, Agent, or Firm* — Winstead PC

(57) ABSTRACT

The present disclosure provides for compositions for the treatment of neurodegenerative diseases comprising one or more isolated phosphate complexes of platinum and methods of uses thereof for treating neurodegenerative diseases including amyotrophic lateral sclerosis, Alzheimer's disease, stroke, epilepsy, Parkinsons, Huntington's disease and diabetes associated peripheral neuropathy The present disclosure is also directed towards an anti-angiogenic composition useful for inhibiting angiogenesis related to age-related macular degeneration, diabetic retinopathy and tumor-associated angiogenesis. An embodiment of the present disclosure is also directed towards a method for modulating the expression of Pigment Epithelial Derived Factor (PEDF) gene in an individual in need thereof. The present disclosure also provides for a method of reducing neurotoxicity associated with the administration of a cancer therapy in a subject in need thereof comprising administering to the individual in need thereof a therapeutically effective amount of at least one or more isolated monomeric phosphate complexes of platinum described herein.

4 Claims, 6 Drawing Sheets

(51) Int. Cl.
| | |
|---|---|
| *A61K 45/06* | (2006.01) |
| *A61K 31/255* | (2006.01) |
| *A61K 31/337* | (2006.01) |
| *A61K 31/427* | (2006.01) |
| *A61K 31/519* | (2006.01) |
| *A61K 31/69* | (2006.01) |
| *A61K 33/24* | (2006.01) |

(56) References Cited

OTHER PUBLICATIONS

Stellmach V, Crawford SE, Zhou W, Bouck N. Prevention of ischemia-induced retinopathy by the natural ocular antiangiogenic agent pigment epithelium-derived factor. Proc Natl Acad Sci U S A. Feb. 27, 2001;98(5):2593-7.

Fitzgerald DP, Subramanian P, Deshpande M, Graves C, Gordon I, Qian Y, Snitkovsky Y, Liewehr DJ, Steinberg SM, Paltán-Ortiz JD, Herman MM, Camphausen K, Palmieri D, Becerra SP, Steeg PS. Opposing effects of pigment epithelium-derived factor on breast cancer cell versus neuronal survival: implication for brain metastasis and metastasis-induced brain damage. Cancer Res. Jan. 1, 2012;72(1):144-53.

Chung C, Doll JA, Gattu AK, Shugrue C, Cornwell M, Fitchev P, Crawford SE. Anti-angiogenic pigment epithelium-derived factor regulates hepatocyte triglyceride content through adipose triglyceride lipase (ATGL). J Hepatol. Mar. 2008;48(3):471-8.

Ramírez-Castillejo C, Sánchez-Sánchez F, Andreu-Agulló C, Ferrón SR, Aroca-Aguilar JD, Sánchez P, Mira H, Escribano J, Fariñas I. Pigment epithelium-derived factor is a niche signal for neural stem cell renewal. Nat Neurosci. Mar. 2006;9(3):331-9.

Yoshida T, Ohno-Matsui K, Ichinose S, Sato T, Iwata N, Saido TC, Hisatomi T, Mochizuki M, Morita I. The potential role of amyloid beta in the pathogenesis of age-related macular degeneration. *J. Clin. Invest.* 115 (10): 2793-800 (2005).

Bose RN, Maurmann L, Mishur RJ, Yasui L, Gupta S, Grayburn WS, Hofstetter H, Salley T. Non-DNA-binding platinum anticancer agents: Cytotoxic activities of platinum-phosphato complexes towards human ovarian cancer cells. Proc Natl Acad Sci U S A. Nov. 25, 2008;105(47):18314-9.

Campochiaro PA, Nguyen QD, Shah SM, Klein ML, Holz E, Frank RN, Saperstein DA, Gupta A, Stout JT, Macko J, DiBartolomeo R, Wei LL. Adenoviral vector-delivered pigment epithelium-derived factor for neovascular age-related macular degeneration: results of a phase I clinical trial. Hum Gene Ther. Feb. 2006;17(2):167-76.

\* cited by examiner

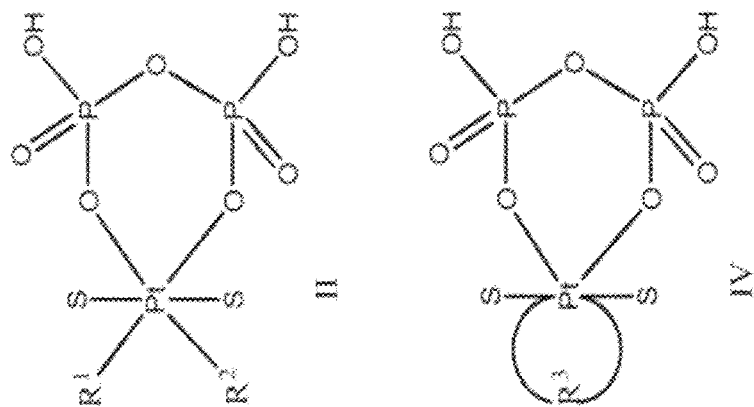
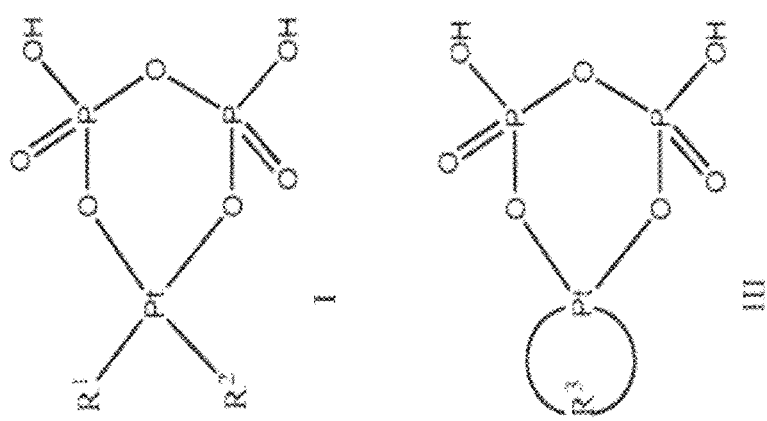
Fig. 1

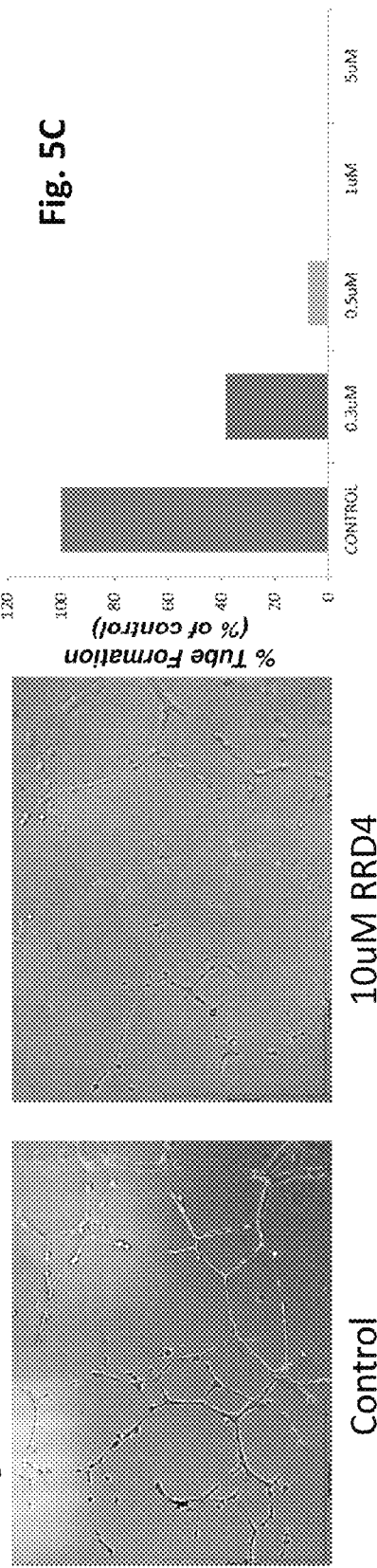
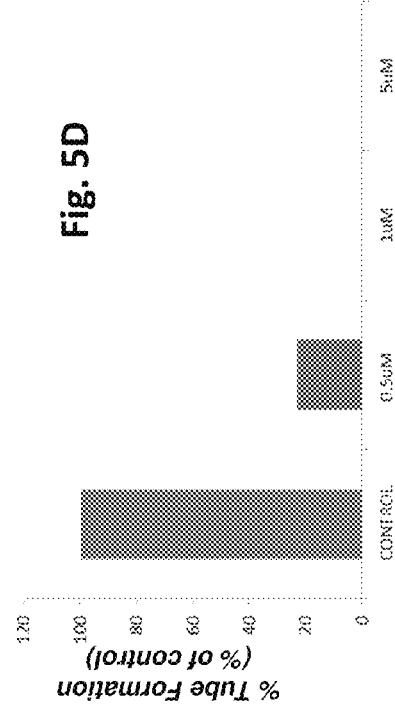
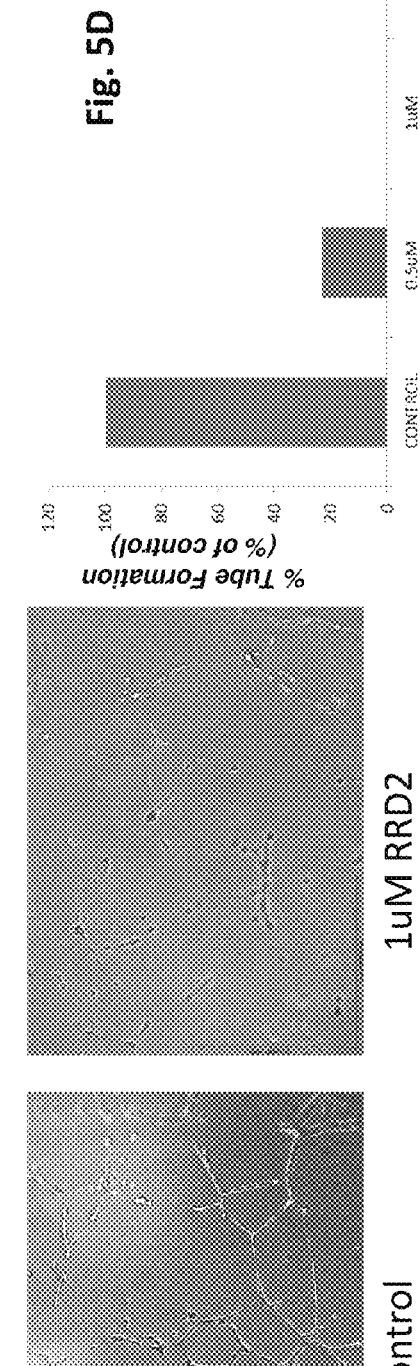

PHOSPHAPLATIN MEDIATED MODULATION OF PIGMENT EPITHELIAL DERIVED FACTOR AND USES THEREOF

CROSS-REFERENCE TO RELATED APPLICATIONS

This application claims priority to U.S. Provisional Application No. 61/768,036 filed Feb. 22, 2013. The entirety of the aforementioned application is incorporated herein by reference.

BACKGROUND

Pigment Epithelial Derived Factor (PEDF), exhibits a number of interesting biological activities, most notably as a potent anti-neovascular or anti-angiogenic agent as well as a neurotrophic factor. The expression of Pigment Epithelial Derived Factor (PEDF) is associated with neuronal differentiation and survival factor for cells derived from the retina and central nervous system (CNS). PEDF has neurotrophic effect on neurons from areas including the cerebellum, hippocampus and spinal cord. Neurotoxicity is also often associated with administration of chemotherapeutic drugs for cancer treatment. Hence, aggressive cancer treatments are limited due to severe neurotoxicity associated with anticancer drugs. PEDF is an attractive target for gene therapy to treat a variety of neurological diseases as well as for treating tumors and other diseases associated with abnormal vascularization, e.g. age-related macular degeneration. However, prior art methods directed towards stabilizing PEDF expression in vivo have met with little success. Therefore, a need exists to develop compositions and methods that would lead to the stable expression of PEDF in vivo.

BRIEF SUMMARY

In some embodiments, the present disclosure provides a composition for the treatment of neurodegenerative diseases comprising one or more isolated platinum complexes of platinum (II) and (IV) having the general formulas as set forth in FIG. 1, wherein $R^1$ and $R^2$ represent monodentate neutral ligands, each independently selected from substituted or unsubstituted aliphatic or substituted or unsubstituted aromatic amines, or a single bidentate neutral ligand $R^3$, replacing both $R^1$ and $R^2$, selected from substituted or unsubstituted aliphatic or aromatic diamines, with $R^1$ and $R^2$ coordinated to the platinum metal center, and wherein when one of $R^1$ and $R^2$ is $NH_3$, the other of $R^1$ and $R^2$ is not $NH_3$, for monodentate ligands, wherein S is independently selected from hydroxide, acetic acid, butyric acid, and alpha-hydroxy acids or charged species thereof coordinated to the platinum metal center. In certain embodiments, $R^1$ and $R^2$ are selected from amine, methyl amine, ethyl amine, propyl amine, isopropyl amine, butyl amine, cyclohexane amine, aniline, pyridine, and substituted pyridine. In certain embodiments, $R^3$ is selected from ethylene-diamine and cyclohexanediamine. In certain embodiments pharmaceutically acceptable salts of the compounds are claimed. Specifically, the composition may be effective in treating neurological diseases selected from amyotropic lateral sclerosis, Alzheimer's disease, stroke, epilepsy, Parkinson's, Huntington's disease, and diabetes associated peripheral neuropathy.

In some embodiments, the composition further comprises a therapeutically effective amount of one or more of the provided complexes and at least one pharmaceutically acceptable carrier such as a carrier, diluent, adjuvant, or vehicle. Specifically, the composition may be effective in treating neurological diseases selected from amyotropic lateral sclerosis, Alzheimer's disease, stroke, epilepsy, Parkinson's, Huntington's disease, and diabetes associated peripheral neuropathy.

Further embodiments of the present disclosure pertain to a method of treating neurodegenerative diseases in a subject in need thereof. Such a method comprises administering to the subject a therapeutically effective amount of at least one of the compositions described above. In some embodiments the method further comprises administering at least one pharmaceutically acceptable carrier, diluent, adjuvant or a vehicle.

Another embodiment of the present disclosure is directed towards an anti-angiogenic composition comprising one or more isolated platinum complexes having the general formulas as set forth in FIG. 1, wherein $R^1$ and $R^2$ represent monodentate neutral ligands, each independently selected from substituted or unsubstituted aliphatic or substituted or unsubstituted aromatic amines, or a single bidentate neutral ligand $R^3$, replacing both $R^1$ and $R^2$, selected from substituted or unsubstituted aliphatic or aromatic diamines, with $R^1$ and $R^2$ coordinated to the platinum metal center, and wherein when one of $R^1$ and $R^2$ is $NH_3$, the other of $R^1$ and $R^2$ is not $NH_3$ for monodentate ligands; and wherein S is independently selected from hydroxide, acetic acid, butyric acid, and alpha-hydroxy acids or charged species thereof coordinated to the platinum metal center.

In certain embodiments, $R^1$ and $R^2$ are selected from amine, methyl amine, ethyl amine, propyl amine, isopropyl amine, butyl amine, cyclohexane amine, aniline, pyridine, and substituted pyridine. In certain embodiments, $R^3$ is selected from ethylene-diamine and cyclohexanediamine. In certain embodiments pharmaceutically acceptable salts of the compounds are claimed. In some embodiments, the composition further comprises a therapeutically effective amount of one or more of the provided complexes and at least one pharmaceutically acceptable carrier such as a carrier, diluent, adjuvant, or vehicle.

In yet, another embodiment, the present disclosure provides a method of inhibiting angiogenesis in a subject in need thereof comprising administering to the subject a therapeutically effective amount of at least one of the compositions described above.

Other embodiments of the present disclosure are directed towards a method for modulating the expression of Pigment Epithelial Derived Factor (PEDF) gene in an individual in need thereof. Such a method comprises administering to the individual a therapeutically effective amount of at least one of the complexes described above.

In still another embodiment of the present disclosure there is provided a method for reducing neurotoxicity associated with the administration of a cancer therapy in a subject in need thereof comprising administering to the individual in need thereof a therapeutically effective amount of at least one of the complexes described above. In some embodiments the cancer therapy is a chemotherapeutic drug. In other embodiments the cancer therapy is radiation. In some embodiments the cancer therapy is administered simultaneously with the at least one of the complexes.

As set forth in more detail below, the compositions and methods of the present disclosure provide for treatment of neurodegenerative diseases via regulation and stabilization of PEDF expression. In addition, the compositions and methods of the present disclosure inhibit angiogenesis related with numerous diseases including cancer.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIG. 1 displays the general formulas for the isolated platinum(II) and (IV) compounds of the present invention.

FIGS. 5A-5D shows inhibition of neovascularization (tube formation) in HUVEC by 1 μM RRD2 (FIGS. 5B and 5C) and 10 μM RRD4 (FIGS. 5A and 5D). The Phosphaplatin compounds inhibited HUVEC tube formation after 30 min of treatment. HUVECs were seeded into 96 well plate pre-coated with 0.1% gelatin and Matrigel, then treated with increasing concentration of the compounds vs. untreated cells. The tube formation was examined by inverted microscope at various timepoints during treatment (magnification 40×).

DETAILED DESCRIPTION

Figure 2:
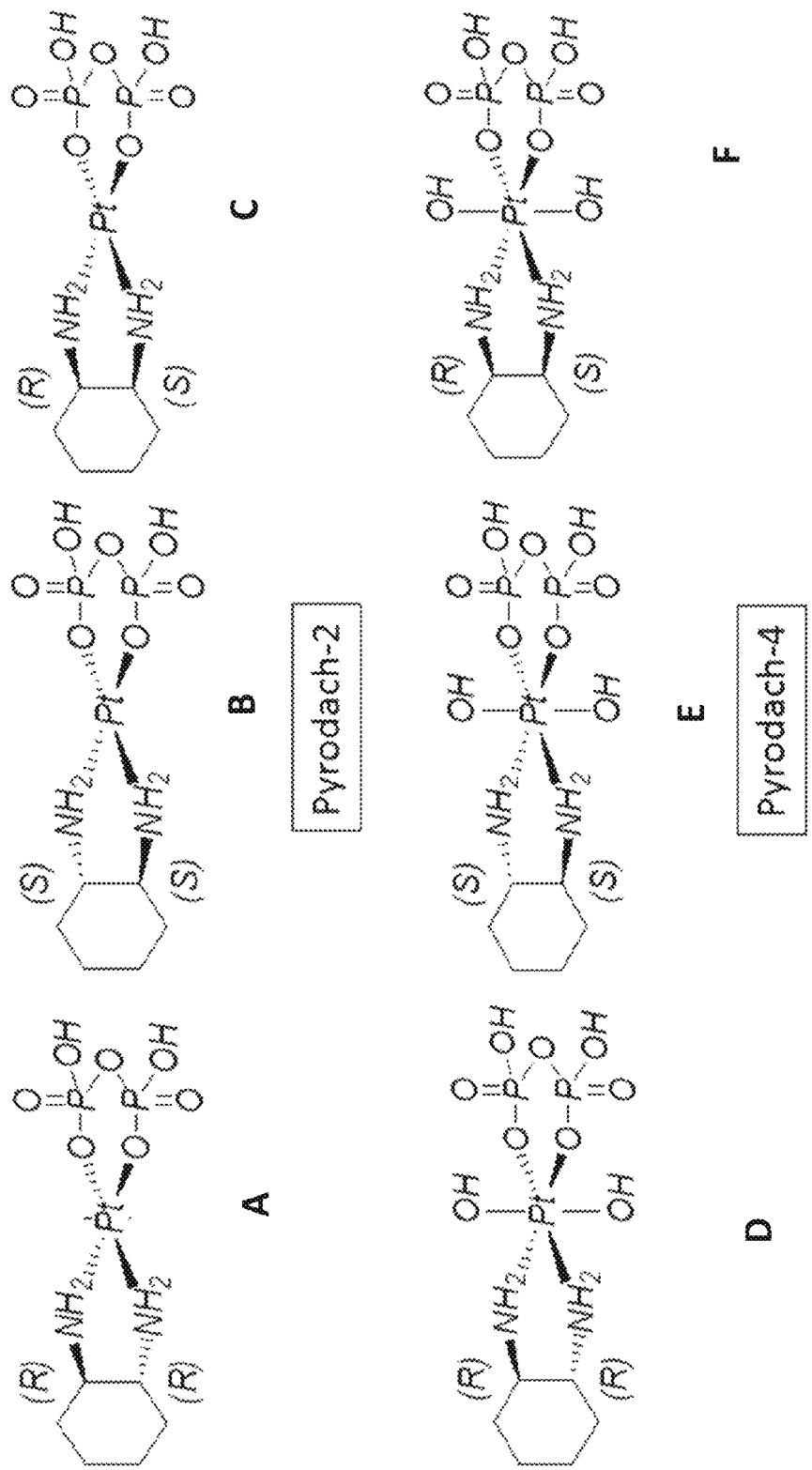
FIG. 2 displays structures of the representative platinum (II) and platinum (IV) complexes of the present invention, namely (A) R,R-trans-1,2-cyclohexane-diamine (dihydrogen pyrophospahto)platinum(II), also known as RRD2; (B) c-S, S-trans-1,2-cyclohexane-diamine (dihydrogen pyrophosphate platinum (IV), (C) R,S-cis-1,2-cyclohexane-diamine (dihydrogen pyrophospahto)platinum(II); (D) R,R-trans-1,2-cyclohexane-diamine-trans-dihydroxo(dihydrogen pyrophospahto) platinum(IV), also known as RRD4; (E) S,S-trans-1,2-cyclohexane-diamine (dihydrogen pyrophospahto) platinum(IV); and (F) S,R-cis1,2-cyclohexanediamine)-trans-dihydroxo(dihydrogen pyrophospahto) platinum (IV).

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims.

The disclosures of all patents, patent applications and publications cited herein are hereby incorporated herein by reference, to the extent that they provide procedural or other details consistent with and supplementary to those set forth herein.

The compounds described herein are useful for the prevention and/or treatment of neurodegenerative conditions including Alzheimer's disease, Parkinson's disease, motor neuron diseases such as amyotrophic lateral sclerosis, and other neurodegenerative diseases.

Additionally, the compounds described herein are also useful for the preventing tumor angiogenesis as well as for the treatment of diseases associated with abnormal vascularization, for e.g. age-related macular degeneration.

Furthermore, the compounds described herein are also useful for treating or preventing chemotherapy-related neurotoxicity.

Pigment Epithelial Derived Factor (PEDF)

Pigment Epithelial Derived Factor is an extracellular 50 kDa secreted glycoprotein originally discovered in cultured fetal retinal pigment epithelial (RPE) cells (Tombran-Tink, J. et al. 1989), and is largely responsible for protecting neurons. PEDF belongs to the serine protease inhibitor (SERPIN) family. However, in contrast to most other SERPINs, which are protease inhibitors, PEDF does not seem to exert an inhibitory action against any of the known proteases. PEDF is produced by retinal pigment epithelial cells and originally was detected at high concentrations within the retina as well as in the vitreous (Dawson, D. W. et al., 1999). PEDF mRNA is found in most tissues, normal cell types (neuronal and non-neuronal) and tumors. This protein is abundant in many human organs as well.

PEDF as a Neuroprotective Factor

Stabilizing the expression of PEDF protein in neuronal cells may potentially enhance neuronal cell survival, for example, as a treatment for neurodegenerative diseases such as amyotrophic lateral sclerosis, Alzheimer's disease, stroke, epilepsy, Huntington's disease, Parkinson's disease, and peripheral neuropathy. Protein neurotrophic factors, or neurotrophins, which influence growth and development of the vertebrate nervous system, are believed to play an important role in promoting the differentiation, survival, and function of diverse groups of neurons in the central nervous system and periphery. The remarkable ability of PEDF protein to provide tremendous protection of neurons against various exogenous and endogenous insults has emerged from decades of research. This protein has shown to prevent ischemia-induced retinopathy (Stellmach V. et al., 2001), diabetic retinopathy, and other neurological disorders (Yabe, T Sanagi et al., 2010). Corneal innervation and reinnervation has been shown to be of major importance in corneal wound healing. In this context, the ability of PEDF to protect spinal motor neurons using a culture model based on a specific defect in glutamate transport in amyotrophic lateral sclerosis (ALS) has been shown. Additionally, PEDF treatment significantly increases the survival of embryonic chock spinal motor neurons in culture in a dose-dependent way, promoting neurite outgrowth of cultured motor neurons and also preventing death of axotomised motor neurons in vivo. The known neurotoxicity of glutamate is considered to be an important mechanism in programmed cell death, and is therefore related to different neurodegenerative disorders. PEDF expression has been shown to inhibit glutamate-induced apoptosis in cerebellar granulae cells. This has been shown to be mediated by activation of the transcription factor NF-kappa B (NF-κB); however, PEDF did not regulate the antiapoptotic genes Bcl-2, Bcl-x and Mn-SOD. This neuro-protective property of PEDF is independent of its role in the inhibition of angiogenesis (Fitzgerald D P et al., 2012).

PEDF as an Anti-angiogenic Factor

PEDF has been shown to be a potent inhibitor of abnormal blood vessel growth of ocular neovascularization (Stellmach V. et al, 2001). PEDF angiostatin has been demonstrated to be a better inhibitor of neovascularization in the mammalian eye, as compared to earlier well-studied antiangiogenic factors. Furthermore, it has been observed that under hypoxic conditions VEGF secretion is high and PEDF expression is low. Intravitreal injection of PEDF has been shown to have protective effects on retinal photoreceptors from morphological and functional deterioration in light-exposed rats. In another model with ischaemic-induced retinopathy in rats, VEGF levels were found to increase to a greater extent than PEDF levels, with a VEGF-PEDF ratio correlating to the observed retinal neovascularisation, suggesting an impaired balance between stimulators and inhibitors of angiogenesis that may contribute to retinal neovascularization.

Furthermore, it has been demonstrated that metastatic cancer patients have either decreased or deleted PEDF protein. Poor prognoses of variety of metastatic cancers including colorectal, lung, ovarian, breast, and others have been directly correlated with the gradual loss of PEDF. In addition to its neurotropic and neuroprotective roles, PEDF has also been implicated as a regulatory factor for various pathways including lipid metabolism (Chung C et al., 2008) and stem cell renewal (Ramirez-Castillejo C. et al., 2006). Moreover, amyloid beta, a peptide largely responsible for the formation of amyloid plaques leading to Alzheimer's disease, has been shown to decrease PEDF mRNA levels (Yoshida T. et al., 2005). Due to its remarkable neuroprotective and antiangiogenic roles, PEDF has been targeted for gene therapy to treat a variety of diseases including macular degeneration (Campochiaro P A et al., 2006) and neuro-degeneration (Yabe T. et al 2010) and metastases. Unfortunately, due to the instability of PEDF gene, such strategy has met with limited success. For example, PEDF transgene expression was found to be stable in cell culture but in vivo expression was lost within few hours in mice models (Fitzgerald D P et al., 2012). Furthermore, the delivery of PEDF gene to brain remains a major challenge.

Phosphaplatins

Phosphaplatins are phosphate bound platinum(II) and platinum(IV) coordination compounds and are described in U.S. Pat. Nos. 7,700,649, 8,445,710, and 8,034,964 and U.S. patent application Ser. No. 13/701,313 and fully incorporated herein by reference. Methods of synthesizing and isolating stable monomeric platinum (II) and (IV) pyrophosphate complexes are also described in U.S. Pat. Nos. 770,649 and 8,034, 694 and U.S. patent application Ser. No. 13/701,313 and fully incorporated herein by reference.

The pyrophosphate coordinated platinum-(II) and -(IV) compounds show excellent antitumor activities against a variety of human cancers as demonstrated by both in vitro (Bose et al., 2008) and in vivo experiments using Scid and Nude mice (Bose et al., 2012). Moreover, these compounds show reduced toxicity compared to other platinum chemotherapeutics that are currently being used as cancer chemotherapies. While the usefulness of various phosphaplatins, as effective anticancer agents, has been reported in the literature, their potential as therapeutic drugs in neurodegenerative diseases, reducing neurotoxicity associated with chemotherapeutic drugs, or as anti-angiogenic agents has not been evaluated or established.

Figure 3:
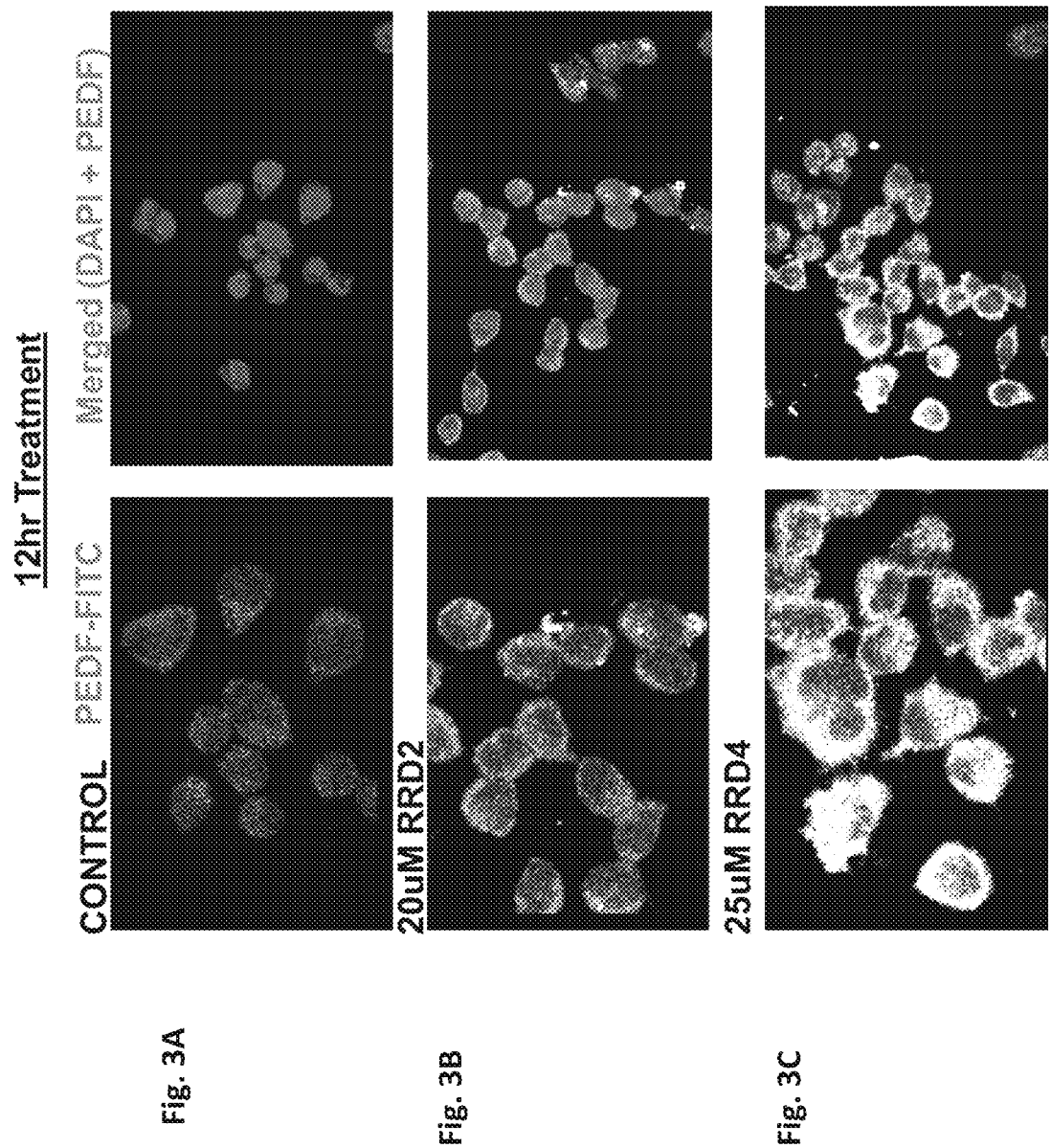
FIGS. 3A-3C show overexpression of PEDF protein (Left panel) as measured by immunofluorescence after 12 hour treatment with 20 μM and 25 μM of compound I and IV in human ovarian cancer cells (A2780). The right panel shows nuclear staining with DAPI.

The present disclosure is directed towards modulating expression of genes involved in neuroprotection, for example, the PEDF gene and its transcription to stably express PEDF protein by administering various doses of various phosphaplatin compounds described in FIG. 1. In particular, treatment of various cells including human umbilical vascular endothelial (HUVEC) and human ovarian cancer cells (A2780) with compounds having the general formulas, I through IV (FIG. 1), yielded over-expression of the PEDF gene from 2- to 5-fold. This overexpression was both concentration and time dependent. For example, treatments of human ovarian cells with phosphaplatin compounds A (referred to as RRD2) and D (referred to as RRD4), as described in FIG. 2, for 3 to 24 hr at 20 and 25 μM concentrations resulted time dependent overexpression. Compound I showed maximum PEDF protein expression after 12 hr treatment while the expression of the protein continue to grow for the compound II beyond 12 hr as revealed from the immune-fluorescence experiments. An example of 12 hr treatment is shown in FIG. 3. The trigger for the overexpression of PEDF depends on multiple cellular mechanisms. For example, the receptor factors for PEDF are known to be phospholipase 2, collagens, integrins, TRAIL, among others. Given the important role of PEDF in mediating neuroprotective effects, the present disclosure is also directed towards compositions effective in treating and methods of treatment for neurodegenerative diseases comprising administering phosphoplatin compounds to subjects in need thereof. Additionally, the present disclosure is also directed towards methods of decreasing neurotoxicity associated with administration of chemotherapeutic drugs in cancer patient. Moreover, the present disclosure discloses methods of preventing angiogenesis and neovascularization in individuals in need thereof. The ability of these phosphaplatin compounds to prevent the formation of blood vessel neovascularization is demonstrated through experiments that indicate the lack of tube formation in HUVEC cells. Details of these experiments are elaborated in Example 4.

Accordingly, one aspect of the present disclosure that will be disclosed in more detail herein provides a composition for the treatment of neurodegenerative diseases. In some embodiments the composition comprises one or more isolated platinum complexes of platinum (II) and (IV) having the general formulas as set forth in FIG. 1, wherein $R^1$ and $R^2$ represent monodentate neutral ligands, each independently selected from substituted or unsubstituted aliphatic or substituted or unsubstituted aromatic amines, or a single bidentate neutral ligand $R^3$, replacing both $R^1$ and $R^2$, selected from substituted or unsubstituted aliphatic or aromatic diamines, with $R^1$ and $R^2$ coordinated to the platinum metal center, and wherein when one of $R^1$ and $R^2$ is $NH_3$, the other of $R^1$ and $R^2$ is not NH$_3$ for monodentate ligands; and wherein S is independently selected from hydroxide, acetic acid, butyric acid, and alpha-hydroxy acids or charged species thereof coordinated to the platinum metal center. In certain embodiments, R$^1$ and R$^2$ are selected from amine, methyl amine, ethyl amine, propyl amine, isopropyl amine, butyl amine, cyclohexane amine, aniline, pyridine, and substituted pyridine. In certain embodiments, R$^3$ is selected from ethylene-diamine and cyclohexanediamine. In certain embodiments, pharmaceutically acceptable salts of the compounds are claimed. In some embodiments, the composition further comprises a therapeutically effective amount of one or more of the provided complexes and at least one pharmaceutically acceptable carrier such as a carrier, diluent, adjuvant, or vehicle.

In an embodiment, the isolated platinum complex is 1,2-Ethanediamine(dihydrogen pyrophosphato)platinum(II). In another embodiment the isolated monomeric platinum complex is (Trans-1,2-cyclohexanediamine)(dihydrogen pyrophosphato)platinum(II). In yet another embodiment, the isolated monomeric platinum complex is cis-diammine-trans-dihydroxo(dihydrogen pyrophosphato)platinum(IV). In yet, still another embodiment, the isolated monomeric platinum complex is 1,2-Ethanediamine-trans-dihydroxo(dihydrogen pyrophosphato)platinum(IV). In some embodiments, the isolated monomeric complex is Trans-1,2-cyclohexanediamine)-trans-dihyroxo(dihydrogen pyrophosphato)platinum (IV). In an embodiment, the composition may be effective in treating neurological diseases selected from amyotropic lateral sclerosis, Alzheimer's disease, stroke, epilepsy, Parkinson's, Huntington's disease, diabetes associated peripheral neuropathy leg and foot ulcerations associated with diabetes, pain and sleep loss induced by diabetes associated neuropathy.

In another embodiment, the present disclosure provides a method of treating neurodegenerative diseases in a subject in need thereof. Such a method comprises administering to the subject a therapeutically effective amount of at least one of the compositions described above. In some embodiments the method further comprises administering at least one pharmaceutically acceptable carrier, diluent, adjuvant or a vehicle. In a related embodiment, the method disclosed herein may be effective in treating neurological diseases selected from amyotropic lateral sclerosis, Alzheimer's disease, stroke, epilepsy, Parkinson's, Huntington's disease, diabetes associated peripheral neuropathy, and leg and foot ulcerations associated with diabetes, pain and sleep loss induced by diabetes associated neuropathy.

Another aspect of the present disclosure relates to an anti-angiogenic composition. In some embodiments the composition comprising one or more isolated platinum complexes of platinum (II) and (IV) having the general formulas as set forth in FIG. 1, wherein R$^1$ and R$^2$ represent monodentate neutral ligands, each independently selected from substituted or unsubstituted aliphatic or substituted or unsubstituted aromatic amines, or a single bidentate neutral ligand R$^3$, replacing both R$^1$ and R$^2$, selected from substituted or unsubstituted aliphatic or aromatic diamines, with R$^1$ and R$^2$ coordinated to the platinum metal center, and wherein when one of R$^1$ and R$^2$ is NH$_3$, the other of R$^1$ and R$^2$ is not NH$_3$ for monodentate ligands; and wherein S is independently selected from hydroxide, acetic acid, butyric acid, and alpha-hydroxy acids or charged species thereof coordinated to the platinum metal center. In certain embodiments, R$^1$ and R$^2$ are selected from amine, methyl amine, ethyl amine, propyl amine, isopropyl amine, butyl amine, cyclohexane amine, aniline, pyridine, and substituted pyridine. In certain embodiments, R$^3$ is selected from ethylene-diamine and cyclohexanediamine. In certain embodiments, pharmaceutically acceptable salts of the compounds are claimed.

In an embodiment, the isolated platinum complex is 1,2-ethanediamine(dihydrogen pyrophosphato)platinum(II). In another embodiment the isolated monomeric platinum complex is (trans-1,2-cyclohexanediamine)(dihydrogen pyrophosphato)platinum(II). In yet another embodiment, the isolated platinum complex is cis-diammine-trans-dihydroxo (dihydrogen pyrophosphato)platinum(IV). In yet, still another embodiment, the isolated platinum complex is 1,2-Ethanediamine-trans-dihydroxo(dihydrogen pyrophosphato)platinum(IV). In some embodiments, the isolated complex is Trans-1,2-cyclohexanediamine)-trans-dihyroxo (dihydrogen pyrophosphato)platinum(IV). In certain embodiments, the composition further comprises an adjuvant, a diluent, a vehicle, or a pharmaceutically acceptable carrier.

In another embodiment, the present disclosure provides a method of inhibiting angiogenesis in a subject in need thereof. Such a method comprises administering to the subject a therapeutically effective amount of at least one of the compositions described above. In some embodiments the method further comprises administering at least one pharmaceutically acceptable carrier, diluent, adjuvant or a vehicle. In a related embodiment, the method disclosed herein may be effective in inhibiting angiogenesis related to age-related macular degeneration or diabetes associated retinopathy, or angiogenesis associated with a tumor.

Another aspect of the present disclosure provides a method for modulating the expression of Pigment Epithelial Derived Factor (PEDF) gene in an individual in need thereof. Such a method comprises administering to the individual a therapeutically effective amount of at least one of the complexes described above. In some embodiments the method further comprises administering at least one pharmaceutically acceptable carrier, diluent, adjuvant or a vehicle. In a related embodiment, the method disclosed herein may be effective in modulating PEDF gene expression to mediate neurotrophic, neuronotrophic, gliastatic or anti-angiogenic effects. Specifically, the method may be effective in inhibiting ocular angiogenesis or neovascularization. In general, the ocular angiogenesis may be caused by age-related macular degeneration or Diabetic Macular edema. The neovascularization may be tumor-associated neovascularization.

In an additional embodiment of the present disclosure there is provided a method of reducing neurotoxicity associated with the administration of a of a cancer therapy in a subject in need thereof. Such a method comprises administering to the individual in need thereof a therapeutically effective amount of at least one of the complexes described above. In some embodiments the method further comprises administering at least one pharmaceutically acceptable carrier, diluent, adjuvant or a vehicle. In an embodiment the cancer therapy being administered is chemotherapy. Specifically, the chemotherapeutic drug is selected from Paclitaxel, Bortezomib, Cyclophosphamide, Eribulin, Mesylate, Ixabepilone, cisplatin, oxiplatin, methotrexate, busulfan, and many others. In another embodiment, the cancer therapy being administered is radiation. In a related embodiment the cancer therapy and the at least one of the complexes are administered simultaneously.

As used herein, a "neurodegenerative disease" refers to a disease in which degeneration occurs of either gray or white matter, or both, of the nervous system. Thus, such a disease can be diabetic neuropathy, senile dementias, Alzheimer's disease, Mild Cognitive Impairment (MCI), dementia, Lewy Body Dementia, Frontal Temporal Lobe dementia, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

The methods of treatment disclosed herein are administered in accordance with good medical practice, taking into account the clinical condition of individual patient, the site and method of administration, scheduling of administration, sex, age, body weight and other factors of the patient. The therapeutically "effective amount", for purposes of treatment herein, are thus determined by such considerations as are known in the art. The amount must be effective to achieve improvement, including but not limited to a more rapid recovery, or improvement or elimination of symptoms and other indicators may be selected as appropriate measures of therapeutically "effective amount" by those skilled in the art.

In the methods of treatment of the present disclosure, the complexes disclosed herein can be administered in various ways. It should be noted that they can be administered as the complex and can be administered alone in aqueous solution taking advantage of the excellent solubility of these complexes, or as an active ingredient in combination with pharmaceutically acceptable carriers, diluents, adjuvants and vehicles. The complexes can be administered orally, subcutaneously or parenterally including intravenous, intraarterial, intramuscular, intraperitoneally, intratonsillar, and intranasal administration as well as intrathecal and infusion techniques. Implants of the complexes are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the complexes of the present disclosure parenterally, they will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propyleneglycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for the compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present disclosure, however, any vehicle, diluent, or additive used would have to be compatible with the complexes.

Sterile injectable solutions can be prepared by incorporating the complexes utilized in practicing the present invention in the required amount of the appropriate solvent with various other ingredients, as desired.

A pharmacological formulation of the present invention can be administered to the patient in an injectable formulation containing any compatible carrier, such as various vehicle, adjuvants, additives, and diluents; or the complexes utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

From the above disclosure, a person of ordinary skill in the art will recognize that the methods and systems of the present disclosure can have numerous additional embodiments. Reference will now be made to more specific embodiments of the present disclosure and experimental results that provide support for such embodiments. However, Applicants note that the disclosure below is for exemplary purposes only and is not intended to limit the scope of the claimed invention in any way.

Example 1

Overexpression of PEDF Gene in Human Cancer Cells

Human ovarian cancer cell lines, A2780 (Fox Chase) were cultured in 100 mm$^3$ plates in monolayer by using RPMI medium 1640 supplemented with 10% FBS, 2 mM glutamine, 0.25 units/mL insulin and penicillin/streptomycin (100 units/ml) in a 37° C. incubator continuously gassed with 5% $CO_2$. The cells were treated with either RRD2 and RRD4, 5 µM and 13 µM, respectively, for 24 hrs in triplicate. The cells were collected by 0.025% trypsin-edta and were centrifuged. The pellet of cells was then resuspended in PBS and washed three times with PBS and pelleted. The total RNA isolated using the Qiagen RNeasy Mini kit (Qiagen Inc.) according to the handbook protocol. The quantity of RNA was measured spectrophotometrically at Absorbance 260 nm ($1 Abs_{260}$=40 ug/ml) and the quality of RNA $A_{260}$:$A_{280}$ ratio was measured between 1.8 to 2.0. For each experiment, 0.9 µg of total RNA was converted to cDNA using the $RT^2$ first strand kit (SABiosciences, Qiagen Inc.) and analyzed on the SABiosciences (Qiagen Inc.) PAHS-024C Human angiogenesis array with an Applied Biosciences 7900HT real-time PCR machine according to manufactures protocol. The threshold cycle (Ct) and baseline for each well was determined by instruments software and the resulting Ct values were analyzed using SABiosciences PCR Array Data Analysis Web-based Software (http://sabiosciences.com/pcrarray-dataanalysis.php). β-Actin and/or GADPH were used as housekeeping gene for determining fold regulation.

Individual Gene expression for PEDF was assessed by two step qRT-PCR assay. First, RNA isolation and purification was done as described above. A total of 2 µg total RNA was used to reverse-transcribe the template into single-stranded cDNA using RT$^2$ first strand kit (SABiosciences, Qiagen Inc.). In the second step, the synthesized cDNA was subjected to qRT-PCR RT$^2$ Primer Set (PEDF) used with SYBR Green real-time PCR master mix detection and endogenous control β-actin and/or GADPH (Applied Biosystems, Foster City, Calif.). All PCR reactions involving cDNA samples from treated and untreated cells were run in triplicate. Quantitative real-time PCR reactions were carried out on the StepOne PCR machine, 48 well system (Applied Biosystems, Foster City, Calif.) according to manufactures protocol. Results were generated using the StepOne software v2.1. The $2^{-\Delta\Delta Ct}$ method was used to present the relative differences in the mRNA expression levels.

TABLE 1

Fold change expression of PEDF after treatment with RRD2 and RRD4, calculated by ΔΔCT method vs the endogenous control β-actin and/or GADPH.

| Compound (treatement) | Fold Change (±SD) | Method of Analysis |
|---|---|---|
| 5 uM RRD-2 (24 hr) | 2.64 | Angiogenesis Array |
| 13 uM RRD-4 (24 hr) | 2.05 | Angiogenesis Array |
| 20 uM RRD-2 (24 hr) | 5.79 | Angiogenesis Array |
| 50 uM RRD-4 (24 hr)* | 4.1 | Single gene expression |
| 25 uM RRD-4 (3 hr)* | 2.1 | Single gene expression |

*endogenous control GADPH was used instead of β-actin.

Example 2

Phosphaplatin Mediated PEDF Protein Expression Determined by Immuno Fluorescence A 6-well plate containing pretreated cover slips was seeded with 500-1000 cells of A2780 human ovarian cancer cell lines in 2.5 ml of RPMI 1640 media (Lonza Walkersville, Frederick, Md.) containing 2.0 mM L-glutamine and supplemented with 10% heat inactivated fetal bovine serum, FBS (Hyclone, Logan, Utah), and 0.25 units/mL recombinant human insulin (Sigma Aldrich, St. Louis, Mo.), 100 U/ml penicillin-streptomycin (Lonza Walkersville, Frederick, Md.). Those cells reaching to 80% confluency were treated with phosphaplatin compounds, RRD2 and RRD4 at various time intervals (3, 6, 12, or 24 hours). Each of the cover slip was washed with PBS three times, and the cells were fixed with freshly prepared 4% paraformaldehyde at room temperature for 20 minutes. The fixed cells were then washed with PBS for three times. These cells were permeablized and blocked with 7.5% bovine serum albumin, BSA/PBS/0.01% triton-X100 at 37° C. for 60 minutes followed by washing the cells with PBS twice. The cover slips were treated with a 1:300 dilution of Pigment epithelium-derived factor (PEDF; also known as serpin F1, SERPINF1) mouse primary antibody (Cell Signalling Technology Inc., Danvers, Mass.) in 7.5% BSA/PBS/0.01% triton for 12-15 hours 37° C. and washed with PBS for three times. The coverslips were incubated with secondary Alexa Fluor 488-conjugated anti-mouse IgG (FITC-Green) (Invitrogen, Carlsbad, Calif.) at a 1:5000 dilution in 7.5% BSA/PBS/0.01% triton-X100 for 1 hour at 37° C. in the dark. The cover-slips were then washed with PBS for another three times. In addition, some treatments were stained for beta-Actin and was stained with Phalloidin (Rhodamine) (Red) (Invitrogen, Carlsbad, Calif.) (7 ul/ml) in 7.5% BSA/PBS/0.01% triton-X100 for 1 hour at 37° C. in the dark. The moist cover-slips were then mounted onto a microscope slide with Ultracruz mounting media containing DAPI (4',6-diamidino-2-phenylindole) (Blue) (Santa Cruz Biotechnology, Santa Cruz, Calif.) (for identifying the nucleus) and images were then collected on an Olympus FV-1000 inverted stage confocal microscope using a Plan Apo N 60×1.42NA oil immersion objective and processed by FluoView software. PEDF protein was found to be overexpressed or upregulated (Left panel) following 12 hour treatment with 20 µM and 25 µM of compound I and IV in human ovarian cancer cells (A2780) (FIGS. 3A-3C).

Example 3

Protein Expression by Western Blot

Figure 4:
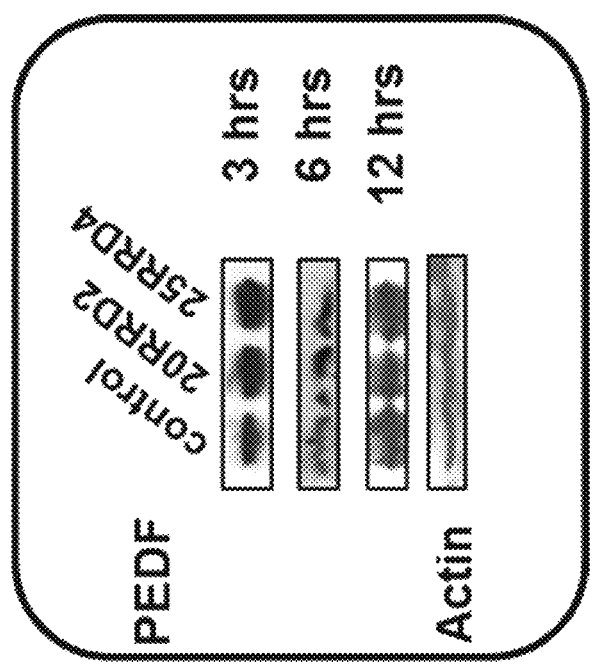
FIG. 4 shows overexpression of PEDF protein as measured by Western Blotting following 3 hrs, 6 hrs, and 12 hrs treatment with 20 μM and 25 μM of compound I and IV in human ovarian cancer cells (A2780). B-actin (used as control) is shown in the bottom most panel.

Treated human ovarian cancer cells (approximately 1×10$^6$ cells in 60 mm$^3$ plates at 80-90% confluence) line with 20 µM RRD2 and 25 µM RRD4 for 3, 6 and 12 hrs was washed with PBS for three times. Total protein was extracted by treating the washed cells directly with 200 µl of RIPA (Sigma, St. Louis, Mo.) or MPER (Pierce, USA). Protein extract samples (50 µg) were separated by 12% SDS-PAGE and blotted onto polyvinylidene difluoride (PVDF) membranes. The blots were washed with TBST [10 mM Tris-HCl (pH 7.6), 150 mM NaCl, 0.1% Tween-20], blocked with 5% skim milk and 1% BSA overnight at 4 C, and incubated with the mouse anit-PEDF (Santa Cruz Biotechnology, USA) primary antibody at 1:500 dilutions in TBST with 5% skim milk and 1% BSA overnight at 4° C. The membrane was then washed TBST, and the primary antibodies were detected with secondary antibody goat anti-mouse IgG conjugated to horseradish peroxidase at 1:2500 dilution for 1.5 hours at room temperature. The blots were developed with enhanced chemiluminescence (ECL) (Pierce, USA) and exposed to X-ray film. The PVDF membranes were stripped with stripping solution (for 1.5 hrs and re-probed with mouse anti-β-actin (Santa Cruz Biotechnology, USA) primary antibody for determining loading. Essentially, PEDF protein expression was upregulated following 3 hrs, 6 hrs, and 12 hrs treatment with 20 µM and 25 µM of compound I and IV in human ovarian cancer cells (A2780) (FIG. 4).

Example 4

Inhibition of Neovascularization of HUVEC Cells by Phosphaplatins: HUVEC Tubulogenesis Assay Endothelial cell tubulogenesis assay was performed seeding 20,000 cells of HUVECs in 96-well plate that was pre-coated with 0.1% gelatin and 40 ul of Matrigel and treated with increasing concentration of phosphaplatin compounds, RRD2 and RRD4 in medium 199 (Lonza Walkersville, Frederick, Md.) supplemented with 20% heat-inactivated FBS (Hyclone, Logan, Utah), 100 µg/ml heparin (Sigma Aldrich, St. Louis, Mo.), 100 U/ml penicillin-streptomycin (Lonza Walkersville, Frederick, Md.) and endothelial mitogen (Biomedical Technologies, Stoughton, Mass.). In brief, Matrigel was defrosted overnight at 4° C. and the 0.1% gelatin coated 96 well plate was chilled and 40 µl of Matrigel was coated into each well. The plate was then incubated at 37° C. and 5% CO$_2$ for 1 hour. The 96-well plate was seeded with 2×10$^4$ cells of HUVECs. After a 24 hour period of cell attachment each well was treated with the increasing concentration of Pt compounds overnight (8-10 hours) at 37° C. and 5% $CO_2$. The capillary/tube formation structures formed were then recorded by an inverted microscope and quantified. Cells were counted in total visual area of 1.575 mm.

To further investigate the anti-angiogenetic behavior of RRD2 and RRD4 on endothelial cell tube formation, we treated HUVECs with different concentration of RRD2 and RRD4 (compounds A and D in FIG. 2) onto Matrigel. After 30 min of incubation with tube-like structures were monitored with an inverted microscope at 40× magnification. Both compounds A and D at 0.5 µM concentrations showed to inhibit more than 85%-90%, respectively, of the ability of HUVEC cells tube formation of on Matrigel assay in a very short period of incubation (FIGS. 5A-5D). No tube formation was evident after a 30 min treatment period.

Example 5

Cell Viability Assay

Promega's CellTiter-Glo® Luminescent Cell Viability Assay was used to determine the number of viable cells in a culture by quantification of ATP (Promega. Madison, Wis.). Briefly, ARPE19 cells, a normal human retinal pigment epithelial cell line, were seeded in a 96 well plate with 10,000-30,000 cells per well and were allowed to attach for 24 hours. Thereafter, the cells were treated with RRD2 or RRD4 at different concentrations ranging from 1 to 100 µM for 24 hours. The detection reagent was prepared per manufactures protocol and equal volume of CellTiter-Glo® reagent was added to each well of cell culture and luminescence read with integration time set for 0.25 to 1 second. The Glo titer Viability Assay has a linear range is from 0 to 50,000 cells per well. Each concentration was done in triplicate.

Figure 6:
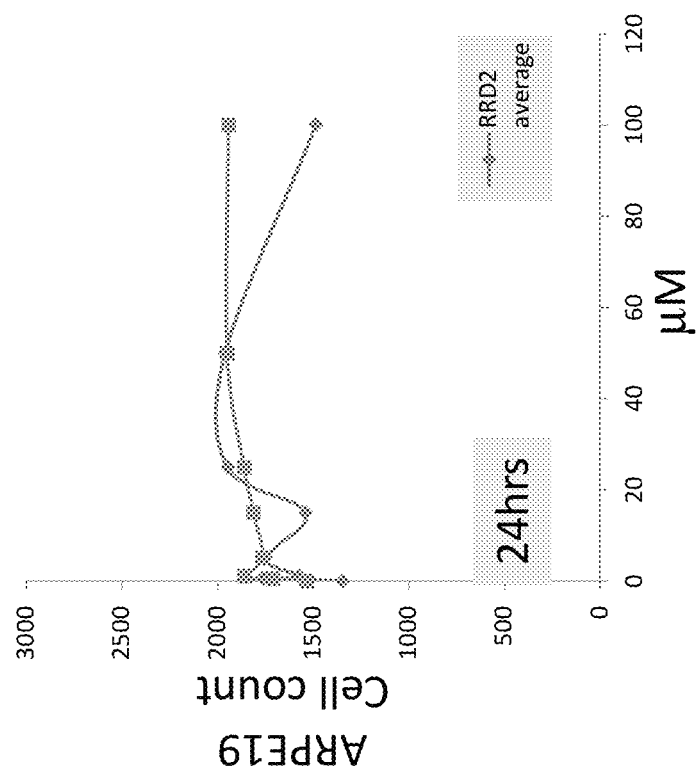
FIG. 6 shows the effects of phosphaplatin compound I (herein referred to as "RRD2") and compound IV (herein referred to as "RRD4") on the viability of normal human retinal pigment epithelial cells. ARPE19 cells were treated with an increasing concentration (ranging from 1 to 100 μM) of RRD2 and RRD4 for 24 hrs and cell viability was measured using Promega's Cell Titer-Glo® Luminescent Cell Viability Assay.

There was no effect on the viability of ARPE19 retinal cells even after 24 hours of treatment with a high dose (100 µM) of either of the phosphaplatins tested (FIG. 6). These results demonstrate that although both RRD2 and RRD4 compounds demonstrate significant anticancer properties at sub-micro molar (<1 µM) concentrations in various human cancer cell lines, i.e. ovarian, colon and prostate, these do not affect the viability of normal cells. These results establish the selective targeting of cancer cells by phosphaplatins.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein

REFERENCES

1. Tombran-Tink J, Johnson L V. Neuronal differentiation of retinoblastoma cells induced by medium conditioned by human RPE cells. Invest Ophthalmol V is Sci. 1989 August; 30(8):1700-7.
2. Dawson D W, Volpert O V, Gillis P, Crawford S E, Xu H, Benedict W, Bouck N P. Pigment epithelium-derived factor: a potent inhibitor of angiogenesis. Science. 1999 Jul. 9; 285(5425):245-8.
3. Tombran-Tink J, Mazuruk K, Rodriguez I R, Chung D, Linker T, Englander E, Chader G J. Organization, evolutionary conservation, expression and unusual Alu density of the human gene for pigment epithelium-derived factor, a unique neurotrophic serpin. Mol Vis. 1996 Nov. 4; 2:11.
4. Stellmach V, Crawford S E, Zhou W, Bouck N. Prevention of ischemia-induced retinopathy by the natural ocular anti-angiogenic agent pigment epithelium-derived factor. Proc Natl Acad Sci USA. 2001 Feb. 27; 98(5):2593-7.
5. Yabe T, Sanagi T, Yamada H. The neuroprotective role of PEDF: implication for the therapy of neurological disorders. Curr Mol Med. 2010 April; 10(3):259-66. Review.
6. Fitzgerald D P, Subramanian P, Deshpande M, Graves C, Gordon I, Qian Y, Snitkovsky Y, Liewehr D J, Steinberg S M, Paltán-Ortiz J D, Herman M M, Camphausen K, Palmieri D, Becerra S P, Steeg P S. Opposing effects of pigment epithelium-derived factor on breast cancer cell versus neuronal survival: implication for brain metastasis and metastasis-induced brain damage. Cancer Res. 2012 Jan. 1; 72(1):144-53.
7. Chung C, Doll J A, Gattu A K, Shugrue C, Cornwell M, Fitchev P, Crawford S E. Anti-angiogenic pigment epithelium-derived factor regulates hepatocyte triglyceride content through adipose triglyceride lipase (ATGL). J Hepatol. 2008 March; 48(3):471-8.
8. Ramírez-Castillejo C, Sánchez-Sánchez F, Andreu-Agulló C, Ferrón S R, Aroca-Aguilar J D, Sánchez P, Mira H, Escribano J, Fariñas I. Pigment epithelium-derived factor is a niche signal for neural stem cell renewal. Nat. Neurosci. 2006 March; 9(3):331-9.
9. Yoshida T, Ohno-Matsui K, Ichinose S, Sato T, Iwata N, Saido T C, Hisatomi T, Mochizuki M, Morita I (2005), The potential role of amyloid beta in the pathogenesis of age-related macular degeneration". J. Clin. Invest. 115 (10): 2793-800.
10. Campochiaro P A, Nguyen Q D, Shah S M, Klein M L, Holz E, Frank R N, Saperstein D A, Gupta A, Stout J T, Macko J, DiBartolomeo R, Wei L L. Adenoviral vector-delivered pigment epithelium-derived factor for neovascular age-related macular degeneration: results of a phase I clinical trial. Hum Gene Ther. 2006 February; 17(2):167-76.
11. Bose R N, Maurmann L, Mishur R J, Yasui L, Gupta S, Grayburn W S, Hofstetter H, Salley T. Non-DNA-binding platinum anticancer agents: Cytotoxic activities of platinum-phosphato complexes towards human ovarian cancer cells. Proc Natl Acad Sci USA. 2008 Nov. 25; 105(47): 18314-9.
12. Bose, 2012 article Bose R. N., Moghaddas S., Majmudar P., Benders D., Dezvareh H, McCall K, and Nislow C. "In Vivo Efficacy and Pharmacodynamics Studies of Non-DNA Binding Platinum Antitumor Agents Phosphaplatins: Evidence for Multiple Cellular Targets" to be submitted to Cancer Research, 2012.

What is claimed is:
1. A method of treating a retinal degenerative disease comprising administering to a subject in need thereof a therapeutically effective amount of a composition comprising at least one isolated monomeric platinum complex of formula A, B, C, D, E or F;

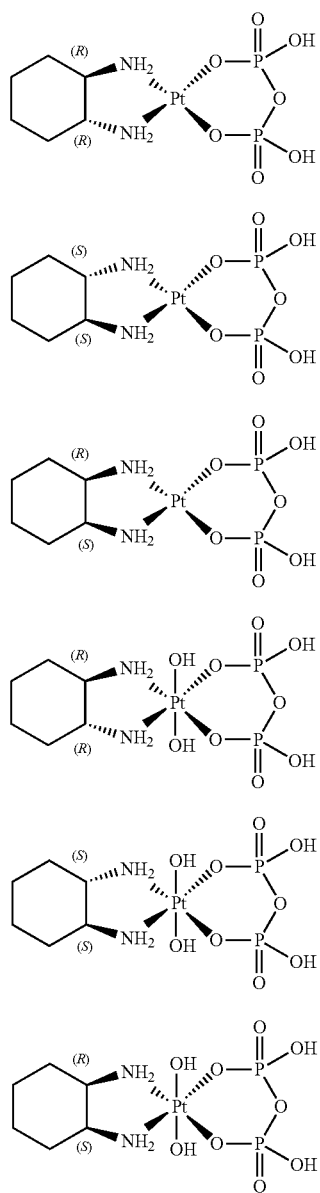

or a pharmaceutically acceptable salt thereof, and at least one pharmaceutically acceptable carrier, diluent, adjuvant, or vehicle; wherein the composition is effective in modulating Pigment Epithelial derived factor (PEDF) gene expression; and wherein the retinal degenerative disease is selected from age-related macular degeneration or diabetes associated retinopathy.

2. The method of claim 1, wherein the administration is intravenously, orally, subcutaneously, intramuscularly, intraocularly or transdermally.

3. A method of modulating the expression of Pigment Epithelial derived factor (PEDF) gene in an individual in need thereof comprising administering to the individual a therapeutically effective amount of a composition comprising at least one isolated monomeric platinum complex of formula A, B, C, D, E or F:

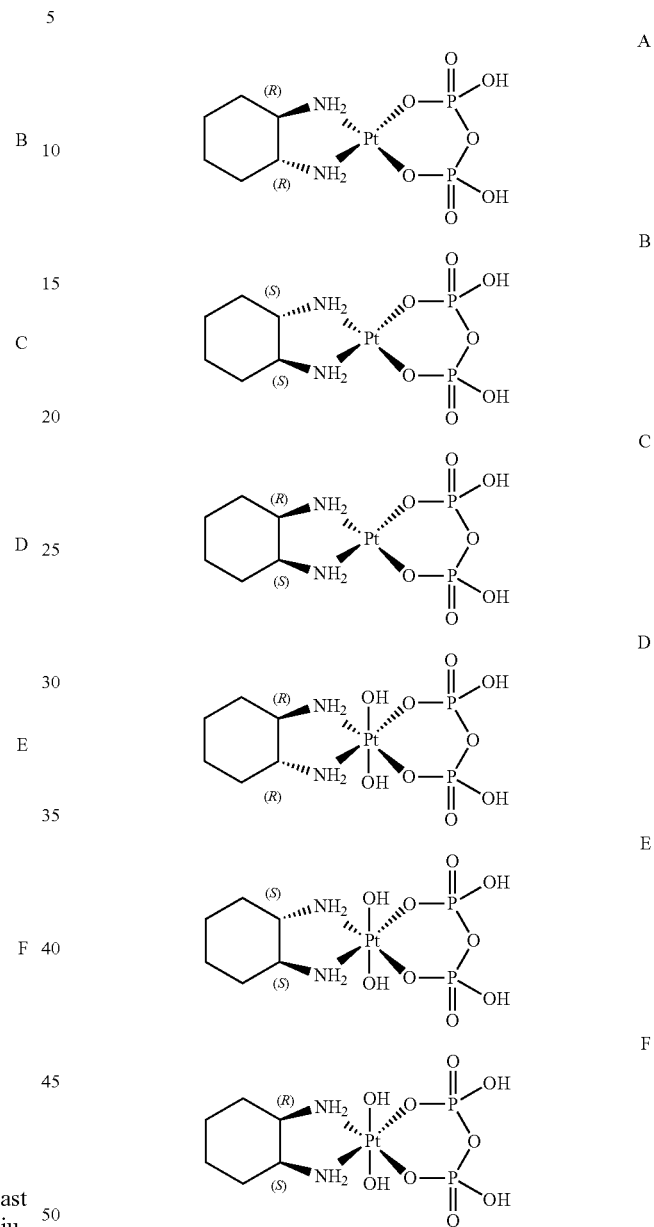

or a pharmaceutically acceptable salt thereof, and at least one pharmaceutically acceptable carrier, diluent, adjuvant, or vehicle; wherein the individual in need thereof is an individual suffering from age-related macular degeneration or Diabetic Macular Edema (DME); and wherein modulation of PEDF gene expression inhibits ocular angiogenesis or ocular neovascularization.

4. The method of claim 3, wherein the modulation of the PEDF gene expression is neurotrophic, neuronotrophic, gliastatic, or anti-angiogenic.

* * * * *